(12) United States Patent
Salomon et al.

(10) Patent No.: US 8,294,333 B2
(45) Date of Patent: Oct. 23, 2012

(54) VIBRATING ROBOTIC CRAWLER

(76) Inventors: Oded Salomon, Kiriat Tivon (IL); Nir Shvalb, Nesher (IL); Moshe Shoham, Hamovil (IL)

(*) Notice: Subject to any disclaimer, the term of this patent is extended or adjusted under 35 U.S.C. 154(b) by 130 days.

(21) Appl. No.: 12/595,620

(22) PCT Filed: Apr. 13, 2008

(86) PCT No.: PCT/IL2008/000505
§ 371 (c)(1),
(2), (4) Date: Jan. 12, 2010

(87) PCT Pub. No.: WO2008/126087
PCT Pub. Date: Oct. 23, 2008

(65) Prior Publication Data
US 2010/0145143 A1    Jun. 10, 2010

Related U.S. Application Data

(60) Provisional application No. 60/907,691, filed on Apr. 13, 2007.

(51) Int. Cl.
*H01L 41/08* (2006.01)
(52) U.S. Cl. .................................................. 310/323.02
(58) Field of Classification Search ............... 310/323.02
See application file for complete search history.

(56) References Cited

U.S. PATENT DOCUMENTS

| | | | |
|---|---|---|---|
| 109,698 A | 11/1870 | Wild et al. | |
| 2,917,762 A | 12/1959 | Xenis | |
| 3,143,895 A | 8/1964 | Robie | |
| 3,196,580 A | 7/1965 | Rakestraw | |
| 3,617,426 A | 11/1971 | Grundman | |
| 3,654,777 A | 4/1972 | Grundman | |
| 3,817,494 A | 6/1974 | Eckerdt | |
| 3,885,356 A | 5/1975 | Armstrong | |
| 3,909,339 A | 9/1975 | Verch | |
| 3,936,044 A | 2/1976 | Kramer | |
| 3,944,457 A | 3/1976 | Podvin | |
| 3,967,828 A | 7/1976 | Topolski | |
| 3,990,933 A | 11/1976 | Verch | |
| 4,400,641 A * | 8/1983 | Vishnevsky et al. | 310/323.02 |
| 4,453,103 A * | 6/1984 | Vishnevsky et al. | 310/323.02 |
| 4,548,090 A * | 10/1985 | Sashida | 74/88 |

(Continued)

OTHER PUBLICATIONS

A.Menciassi et al, "Development of a biomimetic miniature robotic crawler." Auton. Robot I vol. 21(2), p. 155-163, Sep. 2006.

(Continued)

*Primary Examiner* — Mark Budd
(74) *Attorney, Agent, or Firm* — Daniel Feigelson

(57) ABSTRACT

An autonomous vibration-driven device, for motion through a lumen or along a surface, utilizing an array of flexible fibers attached to the body of the device. The outer surface of the fibers have an anisotropic coefficient of friction with the surface along which the device is to move, and the fibers extend from the device body such that at least some of the fibers are in contact with the walls along a part of their length. A transducer is used to vibrate the device, such that it moves down the lumen. The transducer can be either device borne or external. A rotary device is also described, utilizing an array of fibers disposed on the rotor's body, the fibers having an anisotropic coefficient of friction with a central stator or with an outer circular wall. A planar motion device is also described for crawling over a planar surface.

27 Claims, 7 Drawing Sheets

U.S. PATENT DOCUMENTS

| | | | |
|---|---|---|---|
| 4,884,002 A * | 11/1989 | Eusemann et al. | 310/323.02 |
| 4,959,580 A * | 9/1990 | Vishnevsky et al. | 310/323.02 |
| 5,575,378 A | 11/1996 | Billington et al. | |
| 5,770,913 A * | 6/1998 | Mizzi | 310/328 |
| 7,105,987 B2 * | 9/2006 | Witteveen | 310/328 |
| 2005/0085157 A1 | 4/2005 | Dalquist | |

OTHER PUBLICATIONS

A. Gmiterko et al. "In pipe bristled micromachine." Advanced Motion Control, 2002. p. 599-603. 7th International Workshop on Jan. 2, 2002.

PCT Int'l Search Report for WO2008/126087.

T. Hatsuzawa et al. "A linear actuator based on cilia vibration." Sensors and Actuators A 105 (2003) 183-189.

K. Ioi et al. "A Mobile Micro-Robot using Centrifugal Forces." Int'l Confc on Advanced Intelligent Mechatronics, Sep. 19-23, 1999, Atlanta, USA, Proc.IEEE/ASME, 1999, pp. 736-737.

P. Dario, Bioloch, "BIO-mimetic structures for LOComotion in the Human body." Neuro-IT Workshop, Leuven, Dec. 3, 2002, scuola superiore Sant'Anna, http://www.ics.forth.gr/bioloch.

PCT Written Opinion of ISA for WO2008/126087.

PCT International Preliminary Report on Patentability of the ISA for WO2008/126087.

* cited by examiner ically, patents exist for Sublevel 5 in Sonic Scythe mini stage 4 dock

VIBRATING ROBOTIC CRAWLER

This is a 35 U.S.C. §371 application of PCT/IL2008/000505, filed Apr. 13, 2008, and claims the benefit under 35 U.S.C. §120 of said PCT application, and further claims the benefit under 35 U.S.C. §119(e) of U.S. Provisional Patent Application U.S. Ser. No. 60/907,691, filed Apr. 13, 2007. The contents of these priority applications are incorporated herein by reference.

FIELD OF THE INVENTION

The present invention relates to a robotic device for crawling over a surface, whether plane or in a lumen, especially using vibration of the device to propel it by means of flexible fibers having an external surface with anisotropic friction with the surface on which the device is crawling.

BACKGROUND OF THE INVENTION

Current techniques for providing autonomous motion down a lumen generally involve a relatively complicated mechanism with multiple moving parts, which restricts miniaturization because of current technological limitations. Moreover those techniques often require sequential controlled actuations, thus complicating their operation.

Furthermore most methods commonly used cannot operate in confined spaces such as relatively small pipes, or in environments other than those predetermined for the device. Due to the complexity, the multiplicity of moving parts, the possible need of actuators, and control circuits, sensors and internal power sources, prior art mechanisms suffer size limitations, have complex assemblies and relatively high cost, specifically in narrow environments like pipes where miniaturization is essential. More specifically for medical applications, where there is demand for biocompatible miniature systems with a minimal number of moving parts (for medical safety reasons) prior art mechanisms are generally far from optimal.

Hence, there is a need for an autonomous miniature moving mechanism which should be simple, composed of a minimal number of moving parts and which performs well in different environments.

Locomotion inspired by the peristaltic motion of Annelids, and especially of earthworms, has suggested the use of friction between oscillating microstructures and the wall of a lumen or the surface to be traversed. Such devices offer promise for a simple robotic autonomous crawling device.

The paper entitled "Development of a biomimetic miniature robotic crawler" published in Autonomous Robots Journal Vol 21(2) pg. 155-163, describes the development of segmented artificial crawlers endowed with passive hook-shaped frictional microstructures, using a Shape-Memory-Alloy spring which causing its torso to alternately shrink and expand with large amplitude and at low frequencies, thereby, causing locomotion. The hooks provide the anisotropic friction necessary for the progress of the device.

In the paper "In pipe bristled micromachine" published in Advanced Motion Control, 2002, Pg. 599-603, the micromachine locomotion principle is based on a directional friction force between the tips of inclined oscillating bristles and the pipe wall. A small amplitude and high frequency piezoactuator is used in the device torso.

In both of these systems the friction-members limits the contact surface geometry i.e. if applied as an in-pipe moving robot, since no adjusting mechanism is embodied, the diameter range in which such a robot can be applied is narrow. Furthermore, the motion is achieved by changing the distance between two or more anchoring bristles by the use of a size varying actuator such as a Shape-Memory-Alloy or Piezo-electric actuator.

U.S. Pat. No. 2,917,762 for "Apparatus for Traveling through Pipes" to C. P. Xenis, describes an apparatus for in-pipe travel comprised of inclined stiff fibers arranged in a cylindrical manner, having a diameter slightly in excess of the inner diameter of the conduit, and which advances due to vibrations. As described, an inclination angle of about 15 degrees between the fibers and the normal to the longitudinal axis of the apparatus will generate suitable anisotropic friction with the pipe's inner surface while in contact. However the fiber's stiffness and the friction which is induced solely at the tips of the fibers limit the pipe diameter range to which such an apparatus may be applied. In addition this apparatus is limited to uses within a pipe.

U.S. Pat. No. 3,885,356 for "Vibratory Conveyor and Abrader" to J. W. Armstrong describes a conveyer belt system using a vibrating pile material having resilient fibers inclined towards the direction of feed, and vibrated in a direction close to that of the fibers, in order to move objects placed thereupon. This patent describes specific use only of the tips of the vibrating fibers for supporting the load and for providing the motion thereto.

U.S. Pat. No. 5,575,378 for "Transfer Method and Apparatus Therefor" to A. J. Billington et al, describes another vibrating fiber conveyer system, which, instead of fibers, uses a multiplicity of extremely fine and relatively short flexible fibers packed at an ultra high density pile to provide a cushion element for moving a load placed on the fibers. The fibers may also be positioned on an object to move it relative to a base. Use of this fiber construction avoids damage to fragile objects transported by the conveyor.

U.S. Pat. No. 5,770,913 for "Actuators, motors and wheel-less autonomous robots using vibratory transducer drivers" to J. V. Mizzi describes a device providing one of an actuator, motor and a wheel-less autonomous robot using vibratory transducer drivers. The vibratory transducer driver is connected to a reciprocating element, driven reciprocally by the vibration driver. A friction surface is provided for translating reciprocating movement of the reciprocating element into motion. A driven member is moved by contact with the friction surface. This patent suggested a "Fibre-Tran" material supplied by the 3M Company as being a good material for use in the described invention. This material is based on anisotropic friction using the tips of inclined fibers.

Bristle tip-based oscillational crawlers may be limited to specific spatial situations such as pipes having a predetermined diameter and with only small variations in diameter, and moreover to specifically sequential or controlled oscillations. There is a need in the art for an autonomous robot using the vibrational fiber principle, which overcomes some of the disadvantages of previous such devices, and which can comply to a wide and varying range of pipes diameters, and which comprises a minimal number of moving parts, is low in cost and easy to manufacture.

The disclosures of each of the publications mentioned in this section and in other sections of the specification are hereby incorporated by reference, each in its entirety.

SUMMARY OF THE INVENTION

The present disclosure describes an autonomous robotic device and method for crawling along a juxtaposed surface or surfaces using random vibrations. The device utilizes the effects of the vibrations on the anisotropic friction properties between the surfaces along the length of fibers attached to the device, and the surrounding juxtaposed surface or surfaces. The surrounding surface or surfaces may be the inner wall of a lumen, two bounding walls for confined planar motion, a plane on which the device is disposed for two dimensional planar motion or an inner guide wire on which the device crawls. An example of a rotational engine is also shown, based on the same principles of superficial anisotropic friction of fibers attached to the vibrating device.

The robot is generally comprised of a central torso or body, and flexible fibers attached as cantilevers at an angle to the central torso. The fibers should be unloaded if not in contact with any surrounding surface. The fibers should be sufficiently long that, when the device is applied to the inner surface walls of the tube it is intended to negotiate, or to the surface it is intended to crawl along, a portion of the fiber at the end remote from the torso becomes parallel to the surface, making contact with the surface along at least a part of its length. The fibers may have varying flexibility, increasing from base to tip, to enable flexion in such a way as to assist this effect.

The surface of the fibers should have an anisotropic coefficient of friction along at least a portion of their length remote from the torso, such that they grip the opposing surface more strongly in one direction of relative motion than in the other direction. This may be achieved by providing the fibers with spikes extended from their surface, providing contact with surrounding surfaces through the spikes. The fibers are long enough to maintain contact with the surrounding surfaces during motion. The fiber's extended spikes may be slanted at an angle to the fiber, further referred to as the spike angle. The angle between the spikes and the co-operating friction surface, further referred to as contact angle, determines the friction force with the surrounding surface. As a result of the fiber's flexion, the contact angle is approximately equal to the spike angle, allowing the maintenance of an optimal and constant friction force throughout the motion.

The fibers' spikes provide anchoring points to the surrounding surface in the direction opposite to the slant of the spikes, thus stopping backward motion, while enabling slipping movement in their slanted direction, resulting in an anisotropic friction coefficient. The locomotion is optimal when the difference between friction forces acting during movement in opposite directions is maximal. This difference depends both on the difference between the friction coefficients acting in opposite directions, and on the distributed normal forces acting on the contact area with the surrounding surfaces. These two factors depend upon the extent of the contact area of the fibers with their surrounding surfaces and upon the contact angle. Thus a proposed structure having a variable fiber cross section enables optimization of both parameters, maintaining a constant contact angle, a large normal force, and a long parallel contact portion of fiber with the surrounding walls. A particularly simple method of achieving a higher normal force due to a variable flexibility fiber is by use of fibers having a thicker base end than that of the tip end. The base end then provides increased stiffness, and hence increased normal force at the contact end, while the contact end has the desired increased flexibility to make contact with a longer section of the opposing surface.

Since that portion of the fibers making contact with the surrounding surface is parallel to the surrounding surface, the contact angle remains constant throughout the motion. The length of the fibers may be such that they significantly exceed the distance between the device body and the surrounding surface. If the fibers were stiff, as in prior art vibrating bristle devices which rely on bristle tip friction, this would be impractical since the fibers in such devices have only one contact point at the tip of the fiber, and lengthening the fibers would result in a smaller angle of contact at the tip, and reduced friction coefficient. Hence if applied as an in-pipe apparatus, the flexibility of the fibers in the exemplary devices described in the present application, enables application of a single one of such devices to a wide range of diameters. This property makes the invention desirable, for example, for use in medical applications where arteries, the gastrointestinal tract, and other internal lumens may vary greatly in diameter along their length. The considerations above also apply for two bounding walls for confined planar motion, and for rotational movements which are attractive for use in Micro Electro Mechanical System (MEMS) applications, but had been limited till now due to design and manufacturing limitations.

Locomotion is achieved due to random vibrations in any direction or plane applied to the torso of the device. A robot constructed according to these aspects of the present invention progresses due to flexion of its fibers. Thus, any vibration causing the fibers to flex will result in progression. One possible actuation embodiment for such devices is to use an onboard magnet or ferromagnetic slug while inducing a time varying magnetic field upon it. This example enables unlimited operation time, since the activation energy for generating the vibration is provided externally and is not dependent on the use of onboard batteries, while also maintaining simplicity of operation. It is possible to use magnetic induced actuation since the vibration does not need to be controlled in any manner. Any random vibration will enable the device to function correctly. As an alternative to causing the body to vibrate, it is possible to generate the vibrations directly in the fibers, such as by making them of a magnetized or a magnetic material and applying an external alternating magnetic field, or by any other suitable method.

A further implementation includes a method for enabling the robot to move in a two dimensional planar manner. In this case, the fibers are extended downwards, enabling contact with the plane on which the robot is to be applied, resulting in a planar motion.

Other exemplary applications include a method for enabling the robot to move in a planar manner while being confined by two bounding walls. In this case fibers are extended sidewards enabling a planar motion while in contact with the two opposing walls.

Additional implementations include a rotary device which rotates within the walls of a generally round external housing, due to its anisotropic friction fibers and a resulting rotation when vibration is applied to the device. Such a device is most applicable in MEMS technology due to its simplicity and due to the lack of a need for either a shaft axis or a bearing for generating the rotation, though an axis may be needed in order to transfer the rotation to its intended load.

All of the exemplary implementations and examples described in this disclosure illustrating different aspects of this invention, utilize anisotropic friction generated between the fibers and the surface being traversed, based on the friction coefficient between the surface of the fibers and the opposing traversed surface. In order to delineate clearly between this specific type of anisotropic friction and prior art friction arising from interaction between the tips of the fibers and the opposing surface, the frictional property of the surface of the fibers with their opposing surface is generally called superficial anisotropic friction in the present application, and this term is thuswise to be understood throughout the application and as claimed.

One example implementation involves, a vibration-driven device comprising a body having a plurality of flexible fibers attached thereto, the surface of at least some of the fibers having along at least part of their length, anisotropic friction with at least one juxtaposed surface, the fibers extending from the body such that at least some of them are in contact with the at least one juxtaposed surface along part of their length, wherein mutual vibratory motion between the device and the juxtaposed surface causes the device to move relative to the at least one juxtaposed surface.

In such a device, the mutual vibratory motion may arise from a vibration generating system. Such a vibration generating system may comprise an external field which operates on an element disposed in the device. In such a case, the external field may be an alternating magnetic field, and the element disposed in the device may be either a magnetic material or a magnet. Alternatively, the vibration generating system may simply be a transducer disposed on the device. In any of these examples, the vibration generating system may be operative to vibrate the at least one juxtaposed surface. Furthermore, the mutual vibratory motion between the device and the juxtaposed surface may comprise vibration either of the body or of at least some of the fibers.

In any of the above described devices, the at least one juxtaposed surface may be the inside wall of a lumen. This lumen may have either a round or a rectilinear form. Alternatively, the at least one juxtaposed surface may be at least one inside wall of a straight walled conduit.

Additionally, in alternative implementations of any of the above-described devices, the at least one juxtaposed surface may be a planar surface.

Alternatively, the body may be an annular body having a central bore, and the at least one juxtaposed surface may be disposed inside the central bore of the annular body. In such a case, the at least one juxtaposed surface disposed inside the central bore of the annular body may be a guide wire or the external wall of a lumen, and the device may crawl thereal-ong.

Another example implementation can involve a device in which the at least one juxtaposed surface is the inside wall of an annular housing, the device being disposed within the annular housing and the fibers being attached to the body such that they contact the annular housing circumferentially, such that the device rotates within the annular housing.

Alternatively, the body may be an annular body having a central bore, and the fibers may be attached circumferentially to the inside of the central bore, such that the body rotates round a post disposed within the central bore. In such an example, the device may further comprise a linear follower coupled to an outer surface of the annular body, such that the device generates linear motion in the follower.

In those examples where the device crawls within a lumen, the fibers may be attached to the body such that they are all oriented in one direction relative to the axis of the lumen, such that the device moves along the axis of the lumen. Alternatively, the fibers may be attached to the body in groups such that the fibers of one group are oriented in one direction relative to the axis of the lumen, and those of the other group in the opposite direction, the device further comprising a mechanism for deploying and stowing one or the other of the groups of fibers, such that the device can move along the axis of the lumen in either direction according to which group of fibers is deployed.

In such cases of motion through a lumen, the fibers may alternatively be attached to the body in groups, the fibers of a first group being attached to the body on at least one segment on one side of a diametric plane through the cross section of the body, the at least one segment being oriented at a first angle to a line perpendicular to the diametric plane, at least part of some of the fibers being in contact with the inside wall of the lumen, and those of a second group being attached to the body on at least another segment on the opposite side of the diametric plane through the cross section of the body, the at least another segment being oriented at a second angle to a line perpendicular to the diametric plane, the second angle having the opposite sense to the first angle, such that the device performs both rotary and linear motion through the lumen when the mutual vibratory motion is actuated.

Likewise, in the case of a device crawling along the at least one juxtaposed surface, the fibers may be attached to the central bore of the annular body in groups, the fibers of a first group being attached to the body on at least one segment on one side of a diametric plane through the cross section of the body, the at least one segment being oriented at a first angle to a line perpendicular to the diametric plane, at least part of some of the fibers being in contact with the at least one juxtaposed surface, and those of a second group being attached to the body on at least another segment on the opposite side of the diametric plane through the cross section of the body, the at least another segment being oriented at a second angle to a line perpendicular to the diametric plane, the second angle having the opposite sense to the first angle, such that the device performs both rotary and linear motion along the at least one juxtaposed surface when the mutual vibratory motion is actuated.

In either of these previous two exemplary devices, the orientation angles of the segments can be interchanged, such that the direction of linear motion of the device is reversed.

In any of the above described exemplary devices, the anisotropic coefficient of friction with the at least one juxtaposed surface may arise either from spikes disposed superficially along at least some of the fibers or from an anisotropic characteristic of the at least one juxtaposed surface.

Furthermore, the vibratory motion may have a random nature. Additionally, the vibration generating system may be a pulsating lumen.

Other implementations described in this disclosure may relate to a device for autonomous motion through a pulsating lumen, comprising a body having a plurality of flexible fibers attached thereto, the surface of at least some of the fibers having along at least part of their length, anisotropic friction with the inner wall of the lumen, the fibers extending from the body such that at least some of them are in contact with the inner wall of the lumen along part of their length such that pulsation of the lumen causes the device to move along the lumen. In such a device, the pulsating lumen may be either one of a blood vessel of a subject or a portion of the gastro-intestinal tract of a subject.

Even further exemplary implementations described in this disclosure may be for a vibration-driven device comprising a body having a plurality of flexible fibers attached to the body in a spiral form along the body, the surface of at least some of the fibers having along at least part of their length, anisotropic friction with at least one juxtaposed surface, the fibers extending from the body such that at least some of them are in contact with the at least one juxtaposed surface along part of their length, and wherein mutual vibratory motion between the device and the juxtaposed surface may cause the device to move relative to the at least one juxtaposed surface.

In such a device, the at least one juxtaposed surface may be the inner wall of a lumen, such that the device performs both rotary and linear motion through the lumen when the mutual vibratory motion is actuated. In this case, the fibers may be attached to the body in groups, a first group being attached to the body on at least one half segment of the spiral on one side of a diametric plane through the cross section of the spiral, and a second group being attached to the body on at least another half segment of the spiral on the opposite diametric side of the spiral cross section, and wherein the orientation angles which the first and second segments make with a line perpendicular to the diametric plane can be interchanged, such that the direction of motion of the device is reversed.

According to further examples of vibration-driven devices comprising a body having a plurality of flexible fibers attached to the body in a spiral form along the body, as mentioned above, the body may be an annular body having a central bore, and the at least one juxtaposed surface may be either a guide wire or a lumen disposed inside the central bore of the annular body, such that the device may perform both rotary and linear motion along the guide wire when the mutual vibratory motion is actuated.

In such a device, the at least one juxtaposed surface may be the outer wall of the guide wire or lumen, such that the device performs both rotary and linear motion along the guide wire or lumen when the mutual vibratory motion is actuated. In this case, the fibers may be attached to the body in groups, a first group being attached to the body on at least one half segment of the spiral on one side of a diametric plane through the cross section of the spiral, and a second group being attached to the body on at least another half segment of the spiral on the opposite diametric side of the spiral cross section, and the orientation angles which the first and second segments make with a line perpendicular to the diametric plane may be interchanged, such that the direction of motion of the device may be reversed.

BRIEF DESCRIPTION OF THE DRAWINGS

The presently claimed invention will be understood and appreciated more fully from the following detailed description, taken in conjunction with the drawings in which:

DETAILED DESCRIPTION

Figure 1:
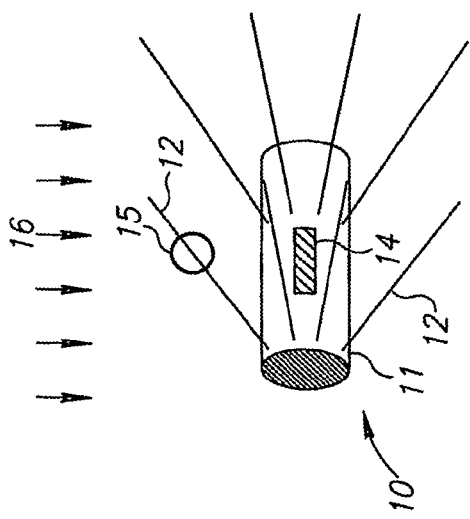
FIG. 1 illustrates schematically a linear motion vibrating robotic crawler constructed and operative according to a first preferred embodiment of the present invention.

Reference is now made to FIG. 1 which illustrates schematically an example of a linear motion vibrating robotic crawler 10 according to one aspect of the present invention. To the body 11 of the device may be attached a number of flexible fibers 12 having superficial anisotropic friction with the opposing surface relative to which the robotic crawler is intended to move. The fibers are attached to the body such that they are generally oriented at angles having the same sense to the axis of the body 11. In FIG. 1, the fibers are all shown oriented to the right of the drawing, meaning that they make an acute angle with the axis in the direction towards the right of the drawing. Although the fibers are all shown inclined at the same attachment angle in FIG. 1, this is not an essential condition for the operation of the device, and it will function so long as a majority of the fibers are generally inclined in one direction relative to a plane perpendicular to the axis of the body. The body of the crawler preferably contains a transducer 14, which, when activated, causes the body to vibrate. There is no requirement that the vibration be in any particular direction for the device to operate, and it can be completely random. The device will also operate, though, if the vibration is of an ordered nature, such as linear, oscillating, reciprocating or circular. The transducer can be self powered, such as by using an internal battery, and the vibration may then be generated by means of a piezoelectric element. Alternatively, the vibration can be activated externally, such as by means of an external AC magnetic field 16 operating on a magnetic slug in the body, or an external AC electric field acting on a dielectric slug in the body.

Figure 2A:
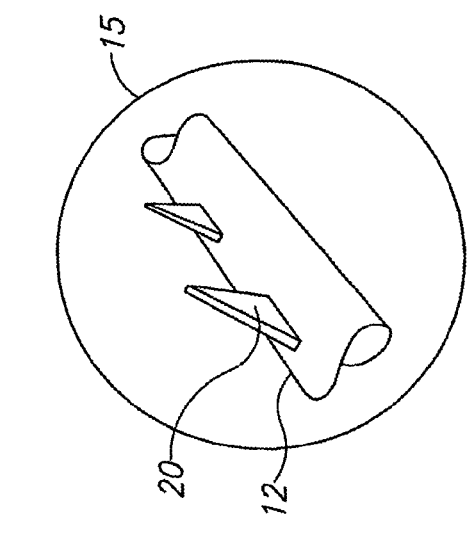
FIG. 2A is an enlarged view of one of the fibers shown in FIG. 1, to illustrate one exemplary manner by which the fibers are given their anisotropic friction coefficient with a surface with which they have contact.

Reference is now made to FIG. 2A, which is an enlarged view of a circled portion 15 of one of the fibers 12 shown in FIG. 1, to illustrate one example by means of which the fibers are given their anisotropic friction coefficient with the surface. The surface of the fiber may be provided with a number of spikes 20 having a sawtooth profile, with the sawteeth inclined in the direction of orientation of the fiber, which, in FIG. 2A is to the top-right of the drawing. When such a spiked fiber brushes against a surface which has a level of roughness such that the points of the spikes can catch in the roughness features of the surface, an anisotropic frictional effect is generated. In the embodiment of FIG. 2A, the fiber can readily move over the surface in a direction towards the bottom-left of the drawing, but not towards the top-right. Alternatively, the fibers can be generally smooth, with only some residual surface roughness, and the anisotropic friction generated by ensuring that the surface on which the fiber is to brush, has features such as the spikes of FIG. 2A, which will enable easy sliding motion in one direction, but not in the reverse direction. This "reversed role" feature is understood to be applicable not only to the example shown in FIG. 2A, but also to all of the exemplary vibratory devices in this application.

Figure 2B:
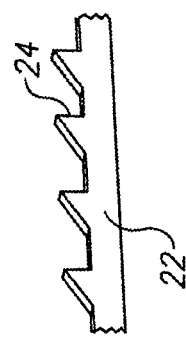
FIG. 2B shows such a fiber, as machined from a thin sheet of metal or etched from a suitable substrate material.

Although the fibers are shown in FIG. 2A as being of round configuration, this is not meant to limit the invention, but they can have any readily available profile preferred. For example, because of the small size of the fibers, according to one example, as shown schematically in FIG. 2B, they can be laser machined from a thin sheet 22, such as by using a finely focused, industrial cutting-mode laser, or by etching from a suitable substrate material. According to this example, the spikes are generated by cutting the fiber profile with integral spikes 24. In such an example, the height of the "fiber" can be as small as a few hundred microns. The fibers may also be fabricated using MEMS or Nano technologies which can result in even smaller dimensions.

Figure 3A:
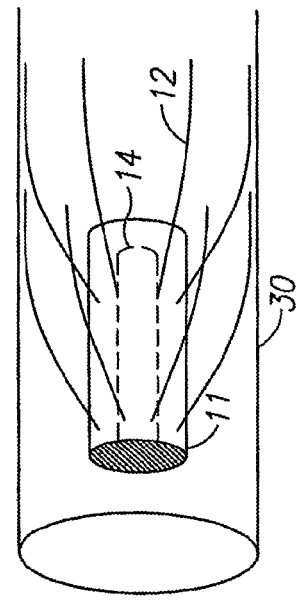
FIG. 3A is a schematic drawing of the crawling device of FIG. 1 inserted into a tube, to illustrate how the device functions.

Reference is now made to FIG. 3A, which is a schematic drawing of the crawling device 10 of FIG. 1 inserted into a tube, 30, to illustrate how the device functions. The radially dispersed locations of the fibers ensure that the device is supported generally near the central axis of tube 30. The vibration transducer 14 causes the device to vibrate when activated, the body undergoing a zig-zag vibrational motion, and this causes the device to move in a direction opposite that of the of the fiber inclination because of the superficial anisotropic frictional effect between the surfaces of the fibers and the tube inner wall. In the example shown in FIGS. 2A, 2B and 3A, the crawler moves to the left. It is clear that the nature of the vibration can be random; all that is required is that at some instants of time, the vibrations cause some of the fibers to move in their low friction direction, until they are latched by means of the spikes in a new location, followed by a similar motion on the opposite side of the device. The spikes remain latched until moved even further in their low friction direction by another vibrational excursion of the same nature. Although the tube in FIG. 3A is shown as a circular tube, it is to be understood that the invention is not limited to this shape, but that the device can negotiate any shaped tube which interacts correctly with the vibrating fibers of the device. In particular, planar geometries, such as are to be found in MEMS applications, can be traversed using fibers attached to the body at two opposite sides to contact the planar walls of a conduit, as will be illustrated below in the embodiment of FIG. 3B.

As an outcome of this mechanism of motion, it is clear that the vibrations do not have to originate in the body of the device, but can be generated by vibration of the fibers themselves, such as could be achieved using ferromagnetic fibers with an alternating magnetic field.

The flexibility of the fibers 12 enables the crawler to fit into lumens of widely varying diameters, with the lumen walls interacting with the parallel portion of the fibers 12 which may be in contact with the wall over a significant part of their length. This enables application of a single-sized device to a wider diameter range of tubes than is possible with prior art devices, which use the tips of bristles against the tube walls to provide the anisotropic friction. This makes the device particularly advantageous for use in medical applications where blood vessels, the gastrointestinal tract, and other internal lumens may vary greatly in diameter along the section to be negotiated by the device. Additionally, the efficiency of motion may be improved due to the large section of each fiber which interacts with the surrounding walls.

According to a further example, the crawler device need not have its own vibration generating mechanism at all, but the vibrations could be generated in the walls of the tube. The embodiment where the tube vibrates longitudinally clearly generates slipping of the fibers along the walls of the tube, and longitudinal motion. However, the wall vibrations may even be directed in a radial direction, perpendicular to the axis of the tube, such that the walls of the tube pulsate in and out, thus causing fibers to lift off and remake contact with the walls in a random manner, and thus to propel the crawling device. Such an embodiment is particularly useful for application in a device for crawling within a blood vessel, where it is the pulsation of the blood vessel which causes the device to move down the vessel.

Figure 3B:
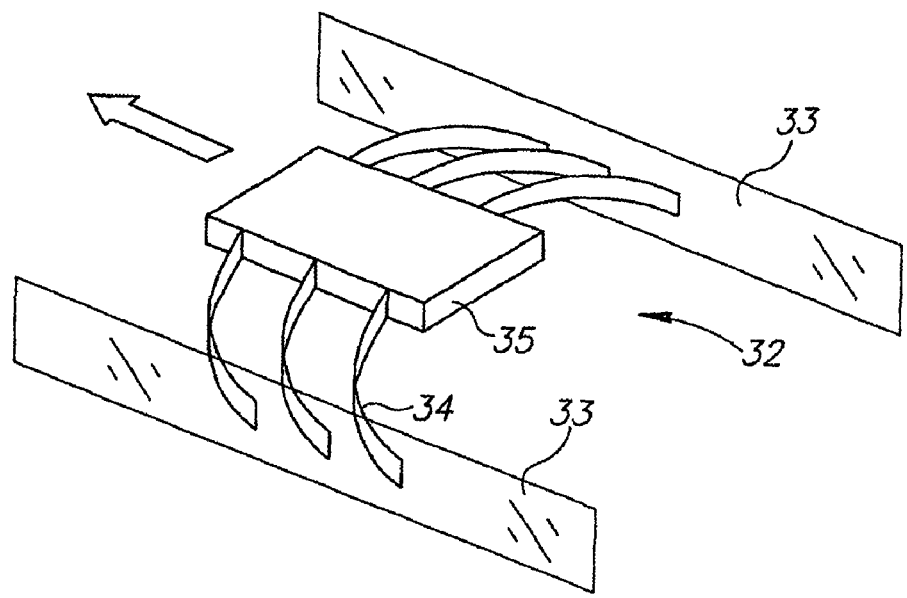
FIG. 3B illustrates schematically a vibratory crawling device for operation in a planar conduit having generally flat side walls.

Reference is now made to FIG. 3B, which illustrates schematically another example of a vibratory crawling device 32 based on the above-described functions, for operation in a planar conduit having generally flat side walls 33. The superficially anisotropic friction fibers 34 contact the rectilinear side walls 33, and propel the body 35 when the device vibrates. Such a planar conduit architecture is common in micromechanical structures, such that this embodiment is particularly useful as a MEMS implementation.

Figure 3C:
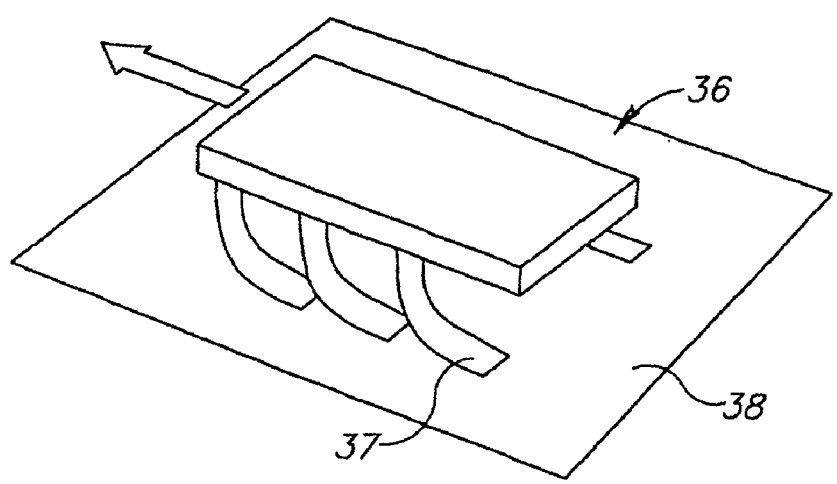
FIG. 3C illustrates schematically a vibratory crawling device for operation on a planar surface.

Reference is now made to FIG. 3C, which illustrates schematically a vibratory crawling device 36 based on the above-described functions, for operation on a planar surface 38. The superficially anisotropic friction fibers 37 are in contact with the planar surface, and as a result of the generally random vibrations of the device, they lift off and remake contact with the planar surface, in some instances landing with their spikes further along the low-friction direction of the planar surface, and thus generate motion in the direction of the arrow.

Figure 4:
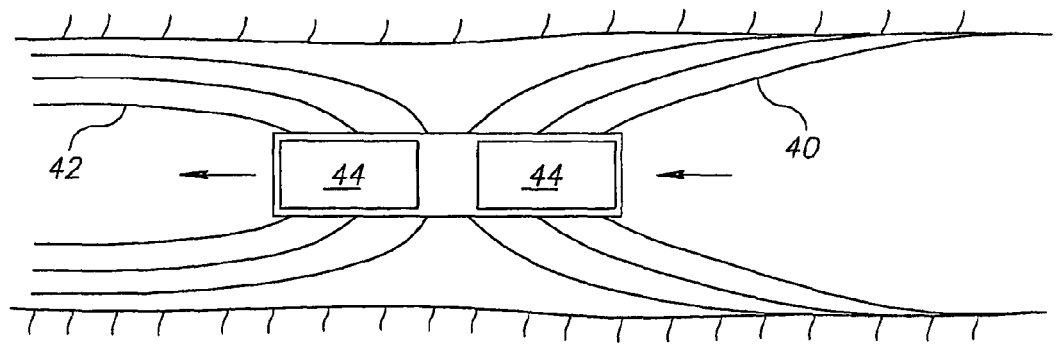
FIG. 4 illustrates schematically a crawling device, based on the example shown in FIG. 3A, but capable of motion in either direction.

Reference is now made to FIG. 4 which illustrates schematically a crawling device, based on the examples shown in FIG. 3, but capable of motion in either direction. The device has two sets of fibers, 40, 42 each oriented in an opposite direction, and a mechanism or mechanisms 44 for either deploying or stowing each set separately. Direction of motion is dependent on which set of fibers is deployed. In the example shown in FIG. 4, the deployed set of fibers 40 generates motion from right to left. Motion in either direction can also be achieved by switching the direction of the fibers, or having different resonating frequencies of the fibers and using different frequencies of vibrations for altering direction of movement of the device.

Figure 5:
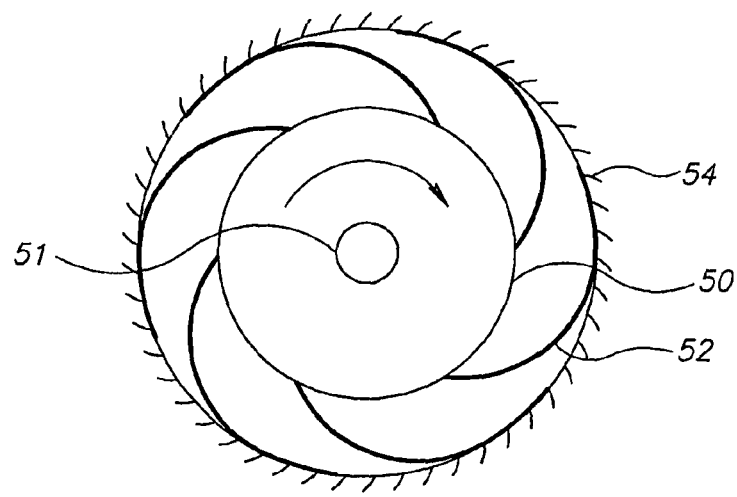
FIG. 5 shows schematically a vibratory anisotropic friction motion device capable of spindle-less rotation.

Reference is now made to FIG. 5, which illustrates schematically a further example of an implementation of the present invention, showing a vibratory superficial anisotropic friction motion device capable of spindle-less rotation. The device has a central body part 50, which may have an onboard vibrational transducer 51, and a number of fibers 52 radiating from the central body, and inclined at an angle other than radially outwards from the body. The fibers should be generally inclined in the same angular direction relative to the radial direction from the body. The device sits within an outer circular wall 54, and the surface of the fibers have an anisotropic coefficient of friction with the walls, as previously explained hereinabove. As the device vibrates, it generates one-way motion of the fibers around the casing wall, thus producing circular motion. For the example shown in FIG. 5, the direction is clockwise. The device needs no axle on which to run, and is simply contained in position within the casing walls. Such spindle-less operation is significantly advantageous for use in MEMS applications, where it is difficult to fabricate a free running rotating device on, for example, a silicon substrate, because of the level of internal rotational friction with a silicon-on-silicon spindle. The exemplary device of FIG. 5 also has significant advantages over prior art circular motors, such as that shown in U.S. Pat. No. 5,770, 913, which requires both a spindle for operation, and a source of externally applied linear oscillations producing reciprocating motion.

Figure 6A:
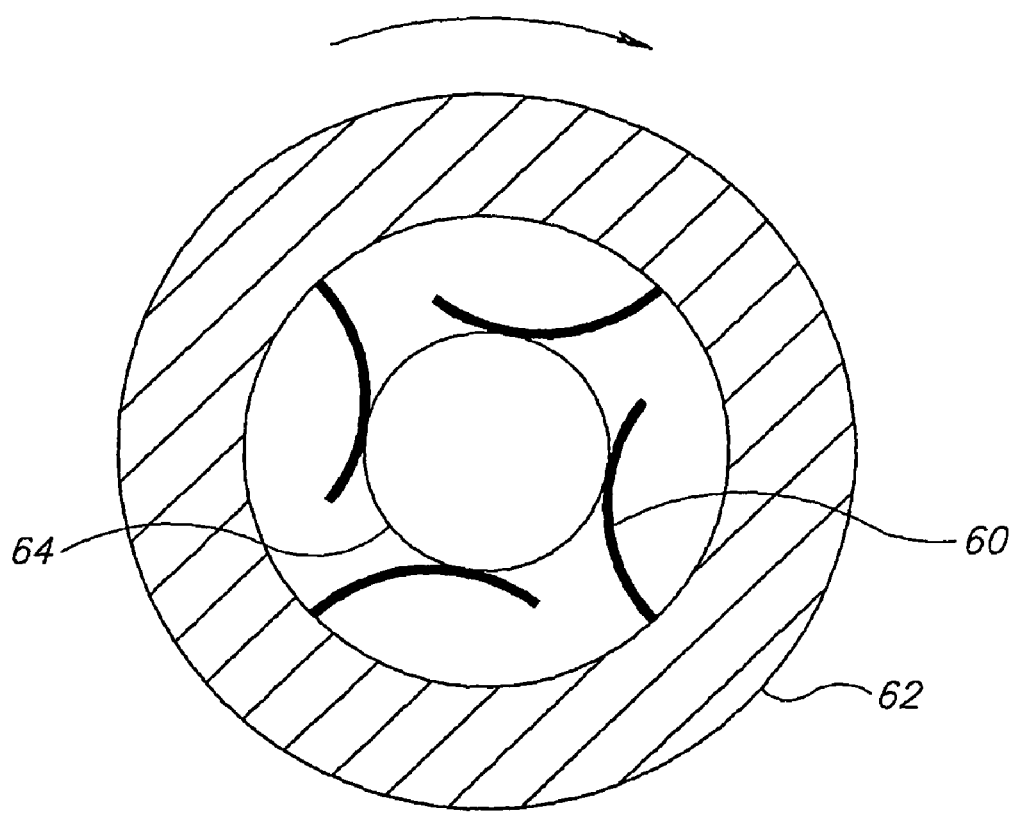
FIG. 6A illustrates schematically a vibratory anisotropic friction motion device, similar to that shown in FIG. 5 except that the flexible fibers are attached internally to an outer rotor which rotates.

Reference is now made to FIG. 6A, which illustrates schematically a further example of an implementation of the present invention, showing a superficial anisotropic friction motion device, similar to that shown in FIG. 5 except that the flexible fibers 60 are attached internally to an outer rotor 62, and the drive surface is in the form of a smaller diameter circular static element 64 disposed within the outer rotor near or at the center of the device. In operation, either the outer rotor or the inner friction surface, or both are vibrated in order to generate the circular motion. Unlike the embodiment of FIG. 5, this embodiment does use a "spindle" for operation, but not in the usual sense of a pivot on which the rotor revolves. In this case, the "spindle" is the central stator element, and only the fibers ride on the stator. Since there is minimal friction in the direction of rotation, it is feasible that this embodiment is readily implementable in silicon for MEMS use. For the embodiment shown in FIG. 6A, the direction is clockwise.

Figure 6B:
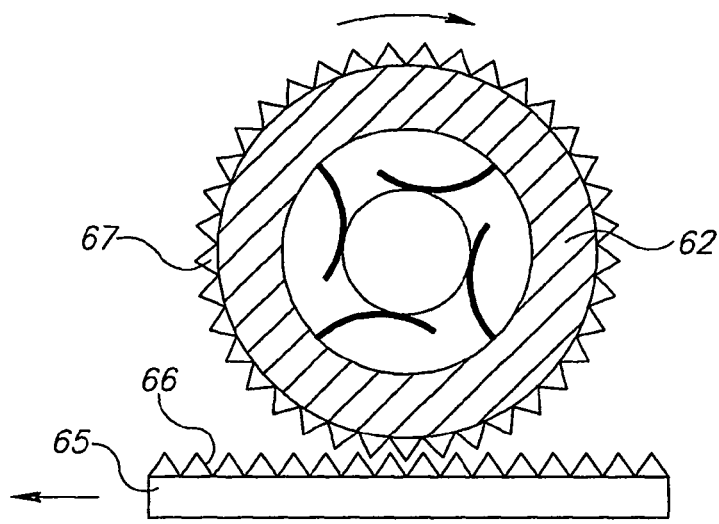
FIG. 6B illustrates the use of the device of FIG. 6A to produce linear motion.

Reference is now made to FIG. 6B, which illustrates schematically a further exemplary implementation of the present invention, showing a preferred use of the embodiment of FIG. 6A to generate linear motion. A linear follower 65, capable of limitless linear movement, is coupled to the rotor 62 of FIG. 6B by means of rack and pinion gears 66, 67. A possible application for such an implementation is in the MEMS field where large linear movements are desired but are difficult to generate. For the example shown in FIG. 6B, the direction of linear motion of the follower 65 is from right to left.

Figure 6C:
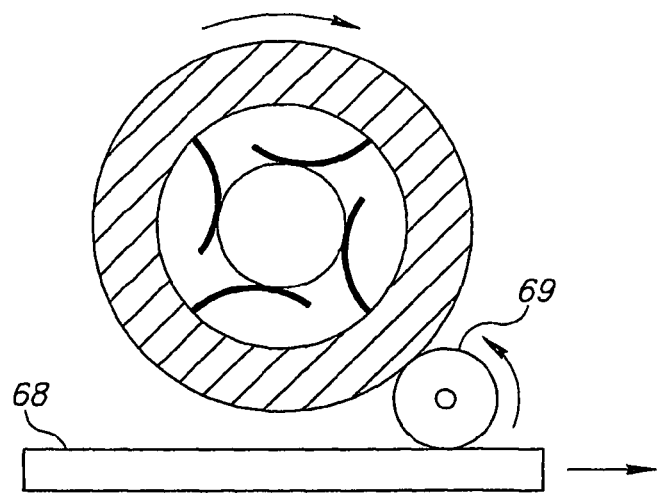
FIG. 6C illustrates the achievement of higher rotational or linear speed, or torque multiplication using the device of FIG. 6A.

Reference is now made to FIG. 6C, which illustrates schematically a further example of a device for achieving higher rotational speed, or higher linear velocity of the follower, or torque multiplication by using the circular motion illustrated in FIG. 6A combined with gear 69 on an idler rotor of different diameter. Rotor 69 may be attached also to a linear follower 68 having a complying gear set to yield a linear motion with a set velocity. For the embodiment shown in FIG. 6C, the direction of rotation of the rotor 69 is counterclockwise and the direction of linear motion of the linear follower is from left to right.

Figure 7:
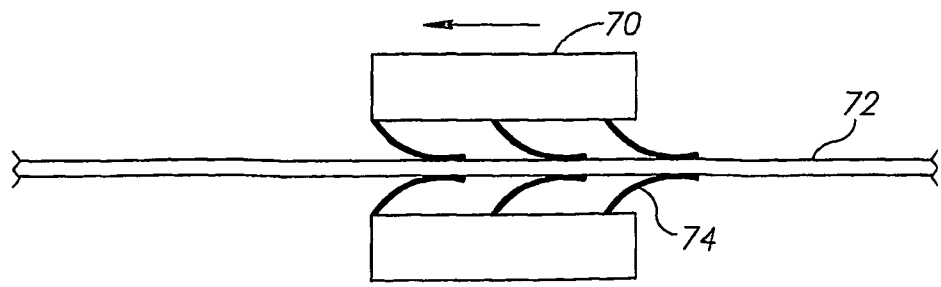
FIG. 7 schematically shows further examples showing a vibration operated crawling device having an annular cylindrical form which can crawl along a central axial element, such as a guide wire.

Reference is now made to FIG. 7, which illustrates schematically a further example for an implementation of the present invention, showing a vibration-operated, superficial anisotropic vibratory crawling device 70 having an annular cylindrical form which can crawl along a central axially arranged element, such as a guide wire 72. The fibers 74 are arranged on the inside volume of the annular cylinder, so as to contact the guide wire along its length, and vibration of the device causes it to crawl along the guide wire. This embodiment is useful for medical applications where a preliminary guide wire is commonly used to define the path of the lumen to be negotiated. For the example device shown in FIG. 7, the direction of motion is from right to left.

Figure 8B:
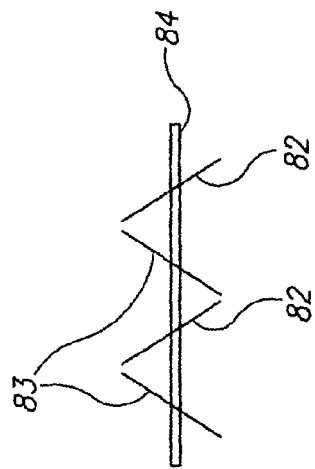
FIGS. 8A to 8D illustrate schematically a further example of a crawling device, which combines linear motion with circular motion.
Figure 8D:
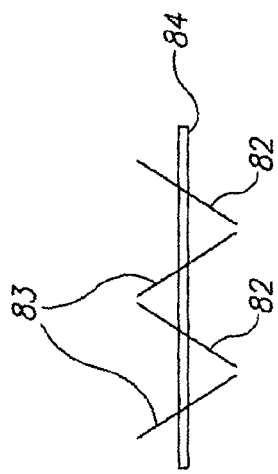
Figure 8A:
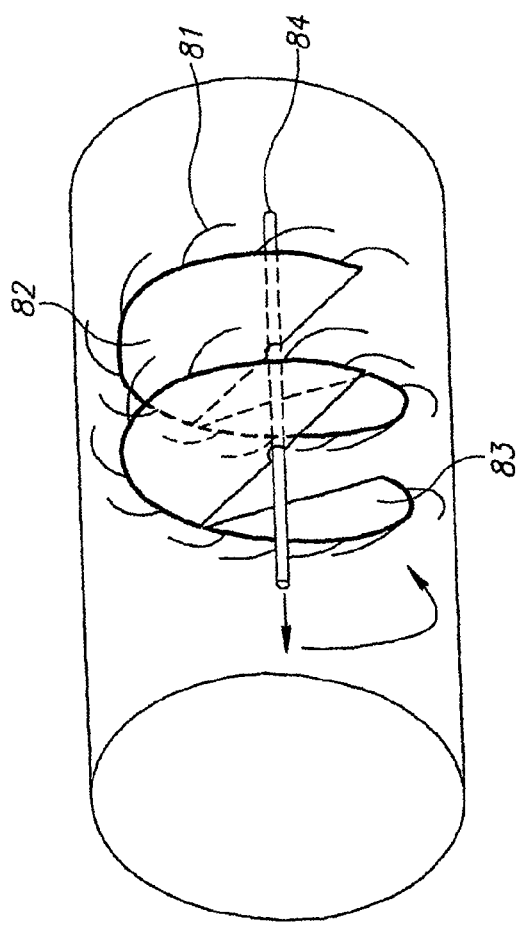

Reference is now made to FIG. 8A which illustrates schematically a further example of a crawling device, which combines linear motion with circular motion, such that the device can be used, for instance, for cleaning the inner walls of the lumen by the rotary motion, and at the same time, proceeding along a lumen. The device is thus suitable for self-propelled internal cleaning of a lumen along the whole length that the device can traverse.

In this example, the fibers 81 are arranged in a generally spiral form along the length of the body 84. The fibers are thus generally aligned at an angle to the axis of the body. Vibration of the body and hence of the fibers thus generates two components of motion between the fibers and the wall of the lumen—one component arising from circumferential contact of the fiber with the wall, and the consequent component of frictional force between the fiber and the wall in a tangential direction, this causing the body to rotate, and a second component arising from the angle which the fibers make with the axis of the body, and the consequent component of frictional force between the fiber and the wall in an axial direction, causing the body to move along the length of the lumen. Such a spiral arrangement of fibers would thus generate rotational and linear motion down the lumen.

Figure 8C:
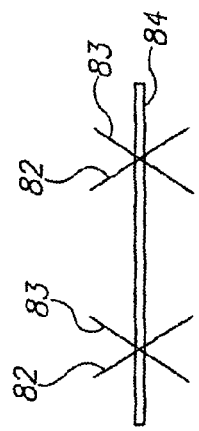

However, it would be useful to enable the direction of linear motion to be reversed, such that in medical applications for instance, the device can be sent in one direction down a lumen, and then retrieved by motion in the reverse direction. This could be achieved by reversing the pitch direction of the spiral, which would result in completely reversed motions. Such an effect can be achieved by viewing the spiral as being slit in half down along its length, and regarding each segment of the split spiral as a separate fiber bearing element, such that the segments on each half of the device can be regarded as semi-discs, whose angle with the body axis can be reversed by means of a mechanical device. Referring again to FIG. 8A, the segments in the top half of the drawing of the device are labeled 82, while those of the bottom half are labeled 83. The segments can be in the form of planes, or as sections of a spiral screw structure. The segments on opposite sides of the spiral split line have angles with opposite inclinations to the axis of the body. By this means, the longitudinal component of the frictional force from the fibers on both groups of segments operate in the same direction. Thus, referring to the exemplary construction shown in FIG. 8A, one segment 82 is inclined at a predetermined angle to the axis of the device such that the inclination of the fibers causes the device to move under vibration from left to right of the drawing. The other segments 83 are inclined at an opposite angle to the axis of the device such that the inclination of the fibers also causes that second segment 83 to move under vibration from left to right of the drawing, The fibers can either be mounted at separate segmental positions on the body, which can also conveniently be alternate positions, as shown in the plan view of the device in FIG. 8B, or fibers can be mounted on two sections of a plane at the same axial position on the device, as shown in FIG. 8C. It is to be understood that the segments do not have to be physical structures, but are used merely to illustrate the positions at which the fibers are attached to the body of the device.

The device shown in the various exemplary implementations in FIGS. 8A to 8C is thus able to traverse a lumen and at the same time to undergo rotational motion, which could be used for a cleaning operation. In order to provide the device with the ability to move in either direction, the angles which the segments make with the axis of the device may be reversed, and the axial motion will reverse its direction. This is shown in the plan view of FIG. 8D, which shows the segments of the example shown in FIG. 8B with their orientations reversed, such that the device will now move from left to right using the parameters and terminology of FIG. 8A. In order to implement such a reversal of angle, it may be convenient to mount the fibers on physical structures, such as sections of disc, so that their planar angle can be readily changed by motion of the angle of these structures. This motion can readily be performed, such as by means of an electro-mechanical miniature mechanism, or a MEMS, which can easily be actuated by wireless when desired, ob by any other mechanism known in the art. The ratio between the rotational speed and the axial speed can be adjusted by changing the angle between the segments and the axis of the body, where smaller angle means lower rotation to axial speed ratio and larger angle means higher rotation to axial speed ratio.

Figure 9:
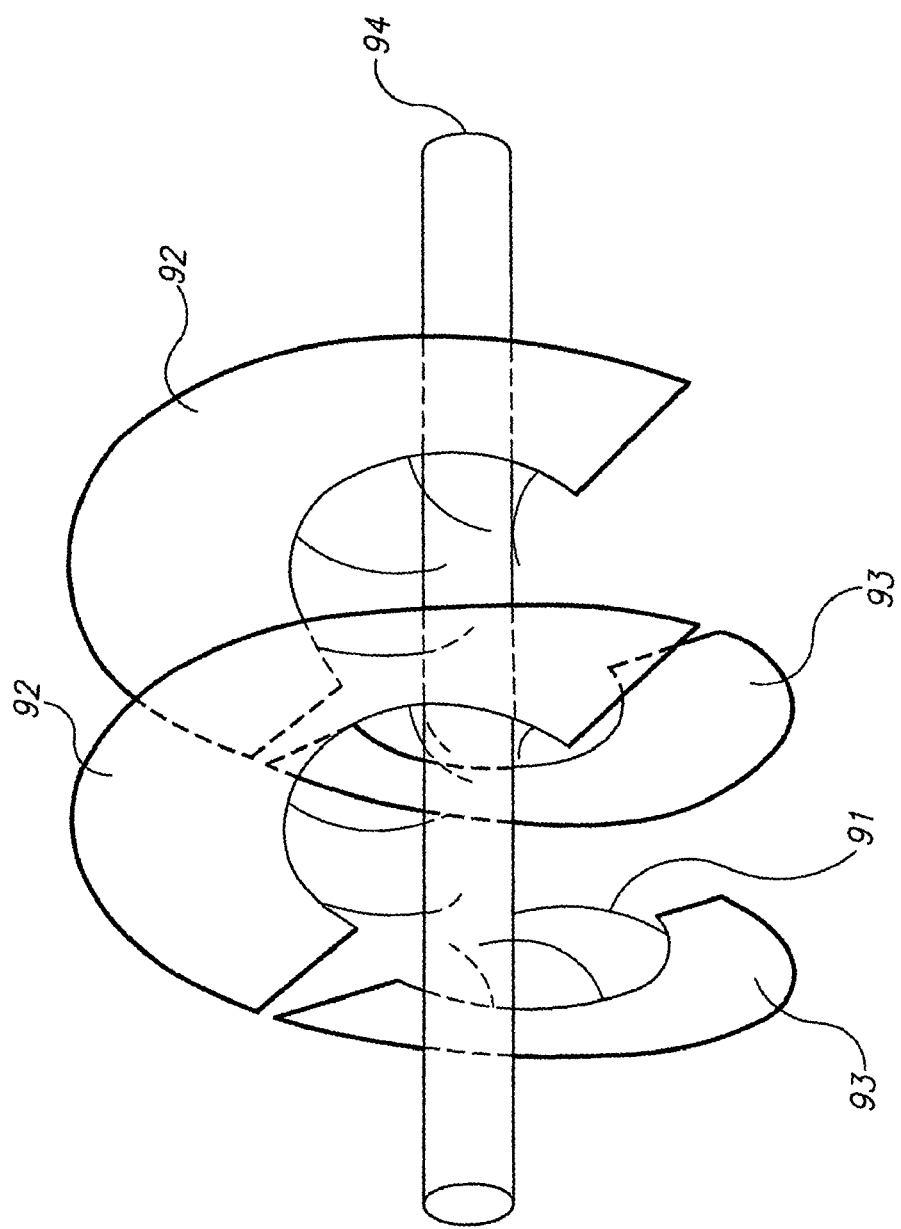
FIG. 9 illustrates schematically a further exemplary device, similar to that of FIGS. 8A to 8D, except that the spiral arrangement of fibers is located on an internal annular wall of the device, such that it can crawl along a guide wire or the outside surface of a lumen, while also rotating.

Reference is now made to FIG. 9, which illustrates schematically a further exemplary device, similar to that of FIGS. 8A to 8D, except that the spiral arrangement of fibers 91 is located on an internal annular wall of the device, such that it can crawl along a guide wire or the outside surface of a lumen 94, while also rotating, such as to clean the surface. In FIG. 9, two sets of segments of the spirally arranged fibers are shown, segments 92 oriented in one direction to the perpendicular to the spiral diametric plane shown, and segments 93 oriented in the opposite direction. As explained regarding the embodiment of FIGS. 8A to 8D, reversal of the orientation angles by means of a mechanical, or other method, results in reversal of the direction of linear motion of the device. FIG. 9 shows only the spatial arrangement of the fibers around the internal bore of the annular body, the other parts of the device being as shown in the previous examples.

The ability of the various examples of the vibrating crawling robot described in this application to move autonomously, and especially those examples suitable for crawling through lumens, provides these devices with the ability to perform a number of tasks, especially in the medical field, which would otherwise be difficult, invasive or impossible. In most of the applications described, the motion of the robot crawler must be controlled to reach the desired target position, or alternatively, if its motion cannot be controlled, such as in fully autonomous applications where the pulsating lumen is the driving force of the device, then the progress of the robot must be monitored, and its operational function activated at a desired target point. One particularly simple method of controlling the navigation of the robot for such applications is by using an externally applied alternating magnetic field. Activation of the desired functions of the robot, can be performed wirelessly, such as by means of electro-mechanical on-board actuation. Descriptions of a number of such applications follow, though it is to be understood that these are only some examples of the potential use of the device, and the invention is not meant to be limited by or to these applications.

(i) Targeted Drug delivery, using a payload of an enzyme or drug for delivery to a specific area. Drug targeting, as opposed to conventional drug delivery, generates high concentrations of the pharmacologically active agent at the relevant patho-physiologically site, resulting in a significant reduction in drug toxicity, reduction of the drug dose, and increased treatment efficacy. Another approach for drug targeting is the delivery of a biologically active agent (enzyme) to the relevant site instead of the actual drug, which reduces the payload volume needed to be carried to the relevant site, and enables interaction with the drug released in the blood for a longer period of time. Use of the vibrating crawling robot described herein enables physical delivery of drugs or enzymes to a desired target in a safe and simple manner. The motion of the robot crawler must be controlled to reach the desired target spot, and the payload must be controlled to be released at a desired target point.

(ii) Vessel occlusion, especially of blood vessels supplying tumors. The doses of chemotherapy necessary to achieve complete tumor eradication may be associated with unacceptably high toxicities. The selective thrombosis of tumor blood vessels has been postulated as an alternative avenue for combating cancer, by depriving tumors of nutrients and oxygen and causing an avalanche of tumor cell deaths. Vascular targeting strategies, aimed at the selective occlusion/disruption of tumor blood vessels, has been shown to have a significant anticancer therapeutic potential and encourage the use of antibody-photosensitizer conjugates for the therapy of superficial tumors and possibly other angiogenesis-related pathologies. Use of a vibrating crawling robot of the type described hereinabove enables such an occlusion or flow disruption to be achieved in a safe and simple manner.

(iii) Intra-coronary arteries pressure and flow sensing. A vibrating crawling robot of the type described hereinabove, may be used to reach a specific target while carrying a sensor payload for locally monitoring a physiological characteristic, such as pressure, flow, glucose levels, or another readily measured parameter. The robot enables targeted and constant monitoring capabilities. It can also be used in other environments besides blood vessels, such as the ureter, parts of the GI tract, and other bodily lumens.

(iv) Infra pulmonary measurements. A vibrating crawling robot of the type described hereinabove can be released from the end of a pulmonary catheter, to reach areas of the lungs which the catheter cannot reach, and to retrieve information from there. The robot is inserted using a catheter that passes through relatively large diameter bodily lumens, such as the bronchial tubes in the lungs, and is then released to negotiate smaller passages which the catheter cannot negotiate, such as the bronchioles.

(v) Intra-cranial motion. This is similar to the previous application in that the robot crawls within the ventricles, for instance to place an electrode or to sense an area.

(vi) Shunt maintenance. A vibrating robot crawler of the type described hereinabove may be used for cleaning cerebrospinal fluid (CSF) shunts used to treat hydrocephalus or normal pressure hydrocephalus patients. The micro robot moves through shunts for cleaning and preventing shunts occlusions, without interfering with the cerebrospinal fluid (CSF) drainage. This use is applicable for any internal shunts intended for long term use, such as Hydrocephalus shunts, urethral catheters, vesicostomy, peritoneal dialysis, and others.

Referring to the example of the CSF shunt, internal hydrocephalus can be successfully treated by placing a drainage tube (shunt) between the brain ventricles and the abdominal cavity to eliminate the high internal pressures. Alternatively, the drainage tube may be introduced into the internal jugular vein through a neck incision. A common complication, generally occurring in the first few months after shunt placement, is shunt blockage due to choroid plexus or blood clots created at the insertion point. A micro robot of the vibrating crawling type described hereinabove, is capable of crawling in tubes, and is ideal for opening occlusions in such shunts, often preventing the need for shunt revision procedures. Alternatively, the device can be used to crawl along their outer surface, possibly using the internal spiral device of FIG. 9, and to clear any occlusions in drainage holes in the shunt or associated tubing.

(vii) Prostate gland treatment. A vibrating robot crawler of the type described hereinabove may be used for reaching the region of the prostate, carrying with it an antenna or other heating device, to apply local heating to remove obstruction of flow.

(viii) Gastro-intestinal monitoring. A vibrating robot crawler of the type described hereinabove may be used for wirelessly monitoring and recording GI movement by traversing through the GI tract, while being able to pause at desired regions, and to go back and forth while taking images from within and collecting biopsies, thus replacing conventional colonoscopy procedures.

(ix) Gastric or GI excitation for obesity or depression treatment. Neural messages carried by the vagus nerve play a significant role in the regulation of ingestion, digestion and satiety. The vagal nerves begin in the brain and extend to multiple organs and regions of the digestive system. Each vagus nerve provides direct two-way communication between the brain and the digestive system without the additional spinal cord processing of impulses that is typical for most other human nerves. The vagal nerve trunks are approximately 3-4 mm in diameter and course along the anterior (front) and posterior (back) of the esophagus before they branch out from the esophagus to the stomach, pancreas, duodenum and gall bladder.

The use of the medical procedure called vagal blocking for obesity control (VBLOC) has successfully demonstrated the ability to decrease the volume of pancreatic exocrine secretions by nearly 90% and to inhibit gastric contractions. This has produced weight loss as a result of reduced calorie ingestion and absorption, early satiation and prolonged satiety.

However VBLOC is an invasive procedure delivered through laparoscopically implanted leads to intermittently block vagal nerve trunks. A vibrating robot crawler of the type described hereinabove may be used for reaching the correct location on the vagus nerves to perform vagal blocking. The autonomous robot may be swallowed as a particularly non-invasive method of deployment, and wirelessly targeted, possibly using an on-board wirelessly actuated transducer, to the vagus nerve in a predetermined location. The robot may encapsulate a neurostimulator which, once the correct location has been reached, will generate electrical stimuli in the form of electrical impulses according to a pre-programmed regimen for the vagus. According to one exemplary implementation of a system for this application, the robot may be in the form of a swallowable pill, including:
(a) Wireless stimulating electrodes.
(b) A degradable (DPS) set of fibers enabling accurate autonomous targeting of the robot.
(c) A degradable anchoring means, to strongly grip the stomach wall, for a limited period of typically up to a month.
(d) An adaptive external control unit for controlling the robot.

(x) ENT applications. A vibrating robot crawler of the type described hereinabove may be used for the insertion of electrodes into the cochlea of the ear, which are otherwise difficult to access non-invasively by conventional means.

(xi) Stent placement. A vibrating robot crawler of the type described hereinabove may be used to restore an open pathway or lumen in a body conduit such as a blood vessel or other body lumen which has become stenosed or occluded. The robot, after reaching the stenosed area, expands in the form of a stent for restoring the stenosed or occluded blood vessel.

(xii) Industrial applications. A vibrating robot crawler of the type described hereinabove may be used in numerous industrial applications where it is necessary to navigate pipes or conduits, especially those having different dimensions along their length. A water, gas or oil leak scanning robot is thus able to navigate and detect leaks within a pipeline having changing diameters.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A vibration-driven device comprising a body having a plurality of flexible fibers attached thereto, the surface of at least some of said fibers having along at least part of their length, anisotropic friction with at least one juxtaposed surface, said fibers extending from said body such that at least some of them are in contact with said at least one juxtaposed surface along part of their length,
wherein mutual vibratory motion between said device and said juxtaposed surface causes said device to move relative to said at least one juxtaposed surface.

2. A device according to claim 1 and wherein said mutual vibratory motion arises from a vibration generating system.

3. A device according to claim 2 and wherein said vibration generating system comprises an external field which operates on an element disposed in said device.

4. A device according to claim 3 and wherein said external field is an alternating magnetic field, and said element disposed in said device comprises either one of a magnetic material or a magnet.

5. A device according to claim 2 and wherein said vibration generating system is either a transducer disposed on said device, operative to vibrate said device, or is a system operative to vibrate said at least one juxtaposed surface.

6. A device according to claim 1 and wherein said at least one juxtaposed surface is either one of the inside wall of a lumen, or is at least one inside wall of a straight walled conduit.

7. A device according to claim 1 and wherein said at least one juxtaposed surface is a planar surface.

8. A device according to claim 1 and wherein said body is an annular body having a central bore, and said at least one juxtaposed surface is disposed inside said central bore of said annular body.

9. A device according to claim 8 and wherein said at least one juxtaposed surface disposed inside said central bore of said annular body is a guide wire or the external wall of a lumen, and said device crawls therealong.

10. A device according to claim 1 and wherein said at least one juxtaposed surface is the inside wall of an annular housing, said device being disposed within said annular housing and said fibers being attached to said body such that they contact said annular housing circumferentially, such that said device rotates within said annular housing.

11. A device according to claim 1 and wherein said body is an annular body having a central bore, and said fibers are attached circumferentially to the inside of said central bore, such that said body rotates round a post disposed within said central bore.

12. A device according to claim 11, further comprising a linear follower coupled to an outer surface of said annular body, such that said device generates linear motion in said follower.

13. A device according to claim 6 and wherein said fibers are attached to said body in groups such that the fibers of one group are oriented in one direction relative to the axis of said lumen, and those of the other group in the opposite direction, said device further comprising a mechanism for deploying and stowing one or the other of said groups of fibers, such that said device can move along the axis of said lumen in either direction according to which group of fibers is deployed.

14. A device according to claim 6 and wherein said fibers are attached to said body in groups, the fibers of a first group being attached to said body on at least one segment on one side of a diametric plane through the cross section of said body, said at least one segment being oriented at a first angle to a line perpendicular to said diametric plane, at least part of some of said fibers being in contact with said inside wall of said lumen, and those of a second group being attached to said body on at least another segment on the opposite side of said diametric plane through the cross section of said body, said at least another segment being oriented at a second angle to a line perpendicular to said diametric plane, said second angle having the opposite sense to said first angle, such that said device performs both rotary and linear motion through said lumen when said mutual vibratory motion is actuated.

15. A device according to claim 8, and wherein said fibers are attached to said central bore of said annular body in groups, the fibers of a first group being attached to said body on at least one segment on one side of a diametric plane through the cross section of said body, said at least one segment being oriented at a first angle to a line perpendicular to said diametric plane, at least part of some of said fibers being in contact with said at least one juxtaposed surface, and those of a second group being attached to said body on at least another segment on the opposite side of said diametric plane through the cross section of said body, said at least another segment being oriented at a second angle to a line perpendicular to said diametric plane, said second angle having the opposite sense to said first angle, such that said device performs both rotary and linear motion along said at least one juxtaposed surface when said mutual vibratory motion is actuated.

16. A device according to claim 14, and wherein the orientation angles of said segments can be interchanged, such that the direction of linear motion of said device is reversed.

17. A device according to claim 1 and wherein said anisotropic coefficient of friction with said at least one juxtaposed surface arises from spikes disposed superficially along at least some of said fibers.

18. A device according to claim 1 and wherein said anisotropic coefficient of friction with said at least one juxtaposed surface arises from an anisotropic characteristic of said at least one juxtaposed surface.

19. A device according to claim 1 and wherein said vibration generating system is a pulsating lumen.

20. A device for autonomous motion through a pulsating lumen, comprising:
a body having a plurality of flexible fibers attached thereto, the surface of at least some of said fibers having along at least part of their length, anisotropic friction with the inner wall of said lumen, said fibers extending from said body such that at least some of them are in contact with said inner wall of said lumen along part of their length such that pulsation of said lumen causes said device to move along said lumen.

21. A device according to claim 20, wherein said pulsating lumen is either one of a blood vessel of a subject or a portion of the gastro-intestinal tract of a subject.

22. A vibration-driven device comprising:
a body having a plurality of flexible fibers attached to said body in a spiral form along said body, the surface of at least some of said fibers having along at least part of their length, anisotropic friction with at least one juxtaposed surface, said fibers extending from said body such that at least some of them are in contact with said at least one juxtaposed surface along part of their length;
wherein mutual vibratory motion between said device and said juxtaposed surface causes said device to move relative to said at least one juxtaposed surface.

23. A device according to claim 22 and wherein said at least one juxtaposed surface is the inner wall of a lumen, such that said device performs both rotary and linear motion through said lumen when said mutual vibratory motion is actuated.

24. A device according to claim 23, wherein said fibers are attached to said body in groups, a first group being attached to said body on at least one half segment of said spiral on one side of a diametric plane through the cross section of said spiral, and a second group being attached to said body on at least another half segment of said spiral on the opposite diametric side of said spiral cross section, and wherein the orientation angles which said first and second segments make with a line perpendicular to said diametric plane can be interchanged, such that the direction of motion of said device is reversed.

25. A device according to claim 22 and wherein said wherein said body is an annular body having a central bore, and said at least one juxtaposed surface is any one of a guide wire or a lumen disposed inside said central bore of said annular body, such that said device performs both rotary and linear motion along said guide wire when said mutual vibratory motion is actuated.

26. A device according to claim 25 and wherein said at least one juxtaposed surface is the outer wall of said guide wire or lumen, such that said device performs both rotary and linear motion along said guide wire or lumen when said mutual vibratory motion is actuated.

27. A device according to claim 26, wherein said fibers are attached to said body in groups, a first group being attached to said body on at least one half segment of said spiral on one side of a diametric plane through the cross section of said spiral, and a second group being attached to said body on at least another half segment of said spiral on the opposite diametric side of said spiral cross section, and wherein the orientation angles which said first and second segments make with a line perpendicular to said diametric plane can be interchanged, such that the direction of motion of said device is reversed.

* * * * *